(12) United States Patent
Anderson et al.

(10) Patent No.: US 8,506,562 B2
(45) Date of Patent: Aug. 13, 2013

(54) DEFLECTABLE STYLET

(75) Inventors: Neil L. Anderson, Roseville (AU); David Ogle, Cowan (AU)

(73) Assignee: Cathrx Ltd., Homebush Bay, NSW (AU)

( * ) Notice: Subject to any disclaimer, the term of this patent is extended or adjusted under 35 U.S.C. 154(b) by 704 days.

(21) Appl. No.: 12/136,707

(22) Filed: Jun. 10, 2008

(65) Prior Publication Data
US 2009/0125001 A1 May 14, 2009

Related U.S. Application Data

(60) Provisional application No. 60/934,736, filed on Jun. 15, 2007.

(51) Int. Cl.
*A61M 25/01* (2006.01)
*A61B 18/18* (2006.01)

(52) U.S. Cl.
USPC ........ 606/41; 604/95.04; 604/95.05; 604/528

(58) Field of Classification Search
USPC ............... 606/32–50; 604/95.04–95.05, 528; 607/101–102
See application file for complete search history.

(56) References Cited

U.S. PATENT DOCUMENTS

| | | | |
|---|---|---|---|
| 3,539,034 A * | 11/1970 | Tafeen | 604/164.09 |
| 4,718,419 A | 1/1988 | Okada | |
| 4,763,647 A * | 8/1988 | Gambale | 600/434 |
| 4,960,134 A | 10/1990 | Webster | |
| 5,125,896 A | 6/1992 | Hojeibane | |
| 5,190,050 A | 3/1993 | Nitzsche | |
| 5,275,151 A | 1/1994 | Shockey et al. | |
| 5,306,245 A | 4/1994 | Heaven | |
| 5,358,479 A * | 10/1994 | Wilson | 604/95.04 |
| 5,364,352 A | 11/1994 | Cimino et al. | |
| 5,395,329 A | 3/1995 | Fleischhacker et al. | |
| 5,441,483 A | 8/1995 | Avitall | |
| 5,454,787 A | 10/1995 | Lundquist | |
| 5,478,330 A | 12/1995 | Imran et al. | |

(Continued)

FOREIGN PATENT DOCUMENTS

DE 36 26 371 2/1987
EP 0 132 344 1/1985

(Continued)

OTHER PUBLICATIONS

European Opinion mailed on Nov. 6, 2009, for European Patent Application No. 08 252 004.0 filed on Jun. 10, 2008, five pages.

(Continued)

*Primary Examiner* — Michael Peffley
*Assistant Examiner* — Khadijeh Vahdat
(74) *Attorney, Agent, or Firm* — TraskBritt

(57) ABSTRACT

A deflectable stylet for a catheter includes an elongate deflectable member with a bend-enhancing region defined at a distal part of the deflectable member. An actuator has a distal end. 1 fast with a distal end of the deflectable member, relative displacement between the actuator and the deflectable member causing deflection of the distal part of the deflectable member at the bend-enhancing region. A control member is displaceably arranged relative to the deflectable member, the control member interacting with the bend-enhancing region of the deflectable member for controlling the extent of deflection of the distal part of the deflectable member.

27 Claims, 6 Drawing Sheets

(56) References Cited

U.S. PATENT DOCUMENTS

| | | | |
|---|---|---|---|
| 5,545,200 A | | 8/1996 | West et al. |
| 5,607,392 A | * | 3/1997 | Kanner .................. 604/86 |
| 5,662,606 A | | 9/1997 | Cimino et al. |
| 5,826,576 A | | 10/1998 | West |
| 5,843,103 A | | 12/1998 | Wulfman |
| 5,861,024 A | | 1/1999 | Rashidi |
| 5,882,333 A | | 3/1999 | Schaer et al. |
| 5,906,627 A | | 5/1999 | Spaulding |
| 5,938,694 A | | 8/1999 | Jaraczewski et al. |
| 6,048,339 A | | 4/2000 | Zirps et al. |
| 6,083,222 A | | 7/2000 | Klein et al. |
| 6,413,234 B1 | | 7/2002 | Thompson et al. |
| 6,551,302 B1 | | 4/2003 | Rosinko et al. |
| 6,666,864 B2 | * | 12/2003 | Bencini et al. .......... 606/41 |
| 7,354,437 B2 | | 4/2008 | Shin et al. |
| 2001/0007070 A1 | * | 7/2001 | Stewart et al. .......... 606/41 |
| 2001/0014770 A1 | * | 8/2001 | Olson et al. ............ 600/374 |
| 2002/0019630 A1 | * | 2/2002 | Falwell et al. .......... 606/41 |
| 2002/0077590 A1 | * | 6/2002 | Ponzi et al. ............ 604/95.01 |
| 2002/0082594 A1 | * | 6/2002 | Hata et al. .............. 606/41 |
| 2003/0014037 A1 | | 1/2003 | Thompson et al. |
| 2003/0069570 A1 | | 4/2003 | Witzel et al. |
| 2003/0109778 A1 | * | 6/2003 | Rashidi .................. 600/374 |
| 2003/0187389 A1 | | 10/2003 | Morency et al. |
| 2003/0208198 A1 | * | 11/2003 | Hayzelden et al. ...... 606/41 |
| 2003/0220676 A1 | | 11/2003 | Helland |
| 2004/0039338 A1 | | 2/2004 | Lee et al. |
| 2004/0116849 A1 | | 6/2004 | Gardeski |
| 2004/0225256 A1 | | 11/2004 | Ponzi et al. |
| 2005/0004515 A1 | * | 1/2005 | Hart et al. .............. 604/95.04 |
| 2006/0084964 A1 | * | 4/2006 | Knudson et al. ........ 606/41 |
| 2006/0184105 A1 | | 8/2006 | Townsend et al. |
| 2006/0224111 A1 | * | 10/2006 | Rosenman et al. ...... 604/95.04 |
| 2008/0045921 A1 | | 2/2008 | Anderson et al. |
| 2010/0137955 A1 | * | 6/2010 | Milijasevic et al. ...... 607/116 |
| 2010/0331776 A1 | * | 12/2010 | Salahieh et al. ........ 604/95.04 |

FOREIGN PATENT DOCUMENTS

| | | |
|---|---|---|
| EP | 1 709 987 A1 | 10/2006 |
| JP | 62-243566 | 10/1987 |
| JP | H04-319365 | 11/1992 |
| JP | 6-232944 | 8/1994 |
| JP | H07-255855 | 10/1995 |
| JP | 9-135905 | 5/1997 |
| JP | 9-285546 | 11/1997 |
| JP | 10-500334 | 1/1998 |
| JP | 11-401 | 1/1999 |
| JP | 2001-0502186 | 2/2001 |
| JP | 2001-505076 | 4/2001 |
| JP | 2001-513692 | 9/2001 |
| JP | 2002-512534 | 4/2002 |
| JP | 7-88093 | 4/2005 |
| WO | WO94/11057 | 5/1994 |
| WO | 95/31243 | 11/1995 |
| WO | 96/37252 | 11/1996 |
| WO | WO98/06337 | 2/1998 |
| WO | 98/38926 | 9/1998 |
| WO | WO-03/090833 A1 | 11/2003 |
| WO | WO-2005/094661 A1 | 10/2005 |
| WO | 2006-012668 | 2/2006 |

OTHER PUBLICATIONS

European Search Report mailed on Nov. 6, 2009, for European Patent Application No. 08 252 004.0 filed on Jun. 10, 2008, three pages.
Australian Search Report for AU Application No. 2008202483, dated Mar. 10, 2011, 2 pgs.
Japanese Office Action mailed on Jan. 11, 2011, for Japanese Patent Application No. 2008-151959, 10 pgs.
Japanese Office Action mailed on Jun. 29, 2010, for Japanese Patent Application No. 2007-557282, filed Mar. 1, 2006, 4 pgs.
International Search Report mailed on May 9, 2006, for PCT Application No. PCT/AU2006/000266 filed Mar. 1, 2006, 5 pgs.
Supplementary European Search Report completed Jun. 7, 2010, for European Patent Application No. 06 70 4940, 6 pgs.

* cited by examiner

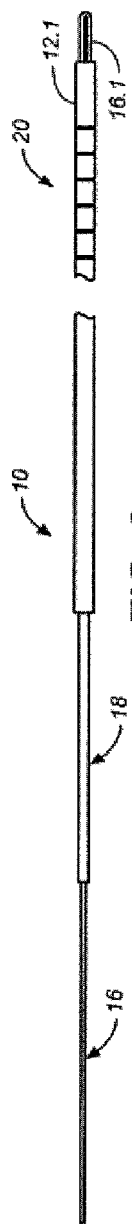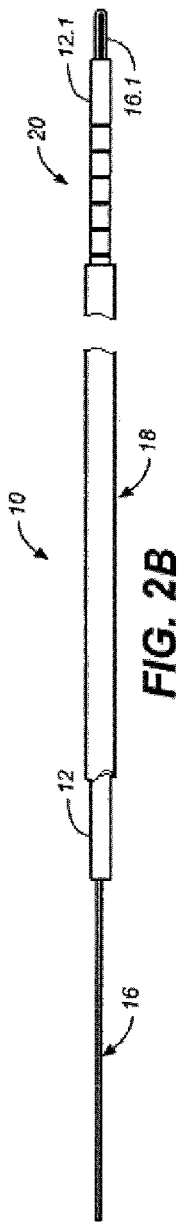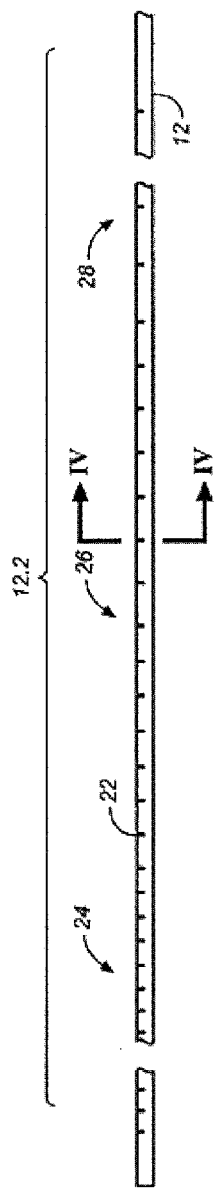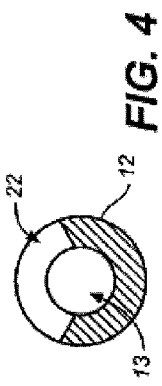

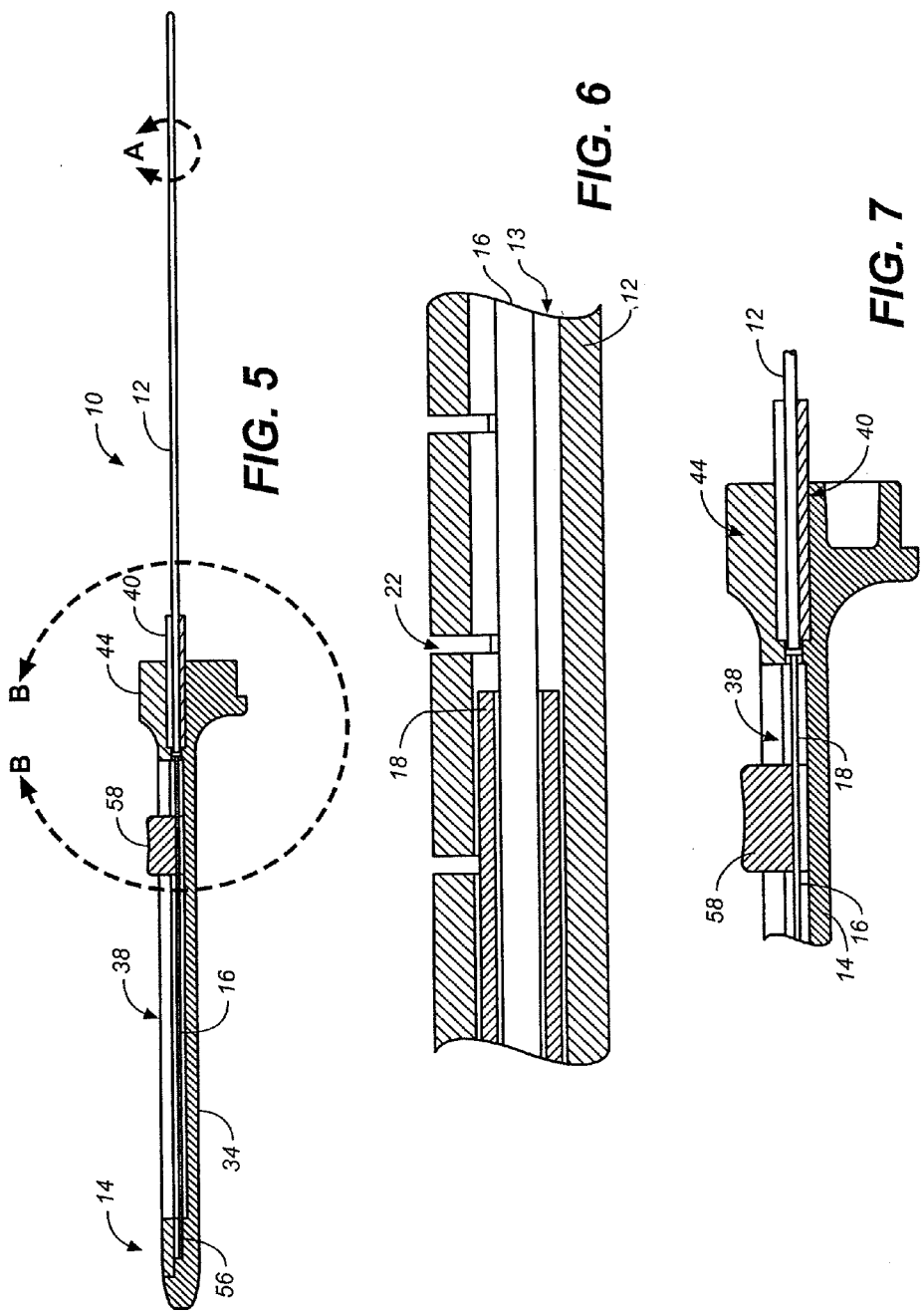

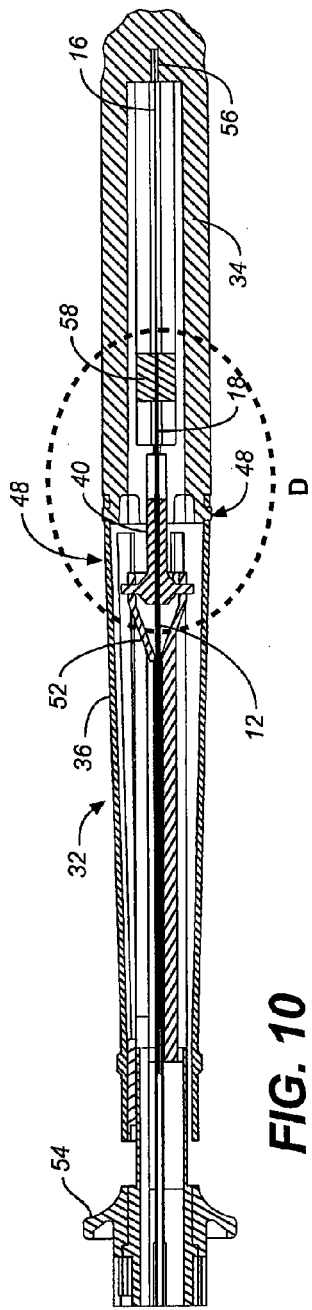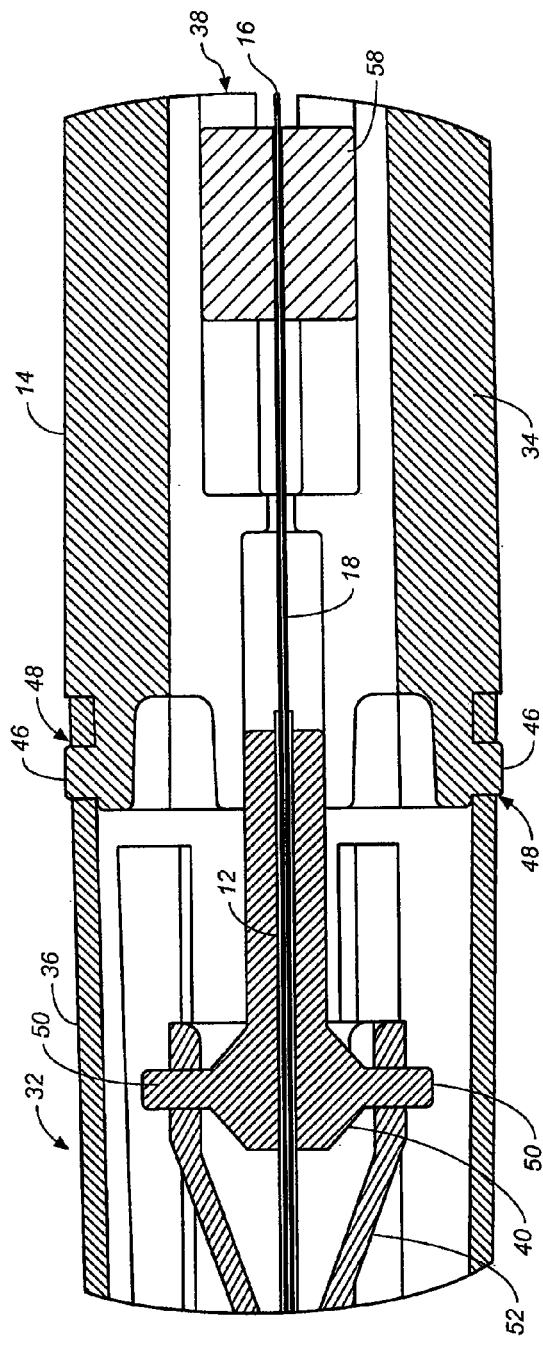

DEFLECTABLE STYLET

CROSS-REFERENCE TO RELATED APPLICATIONS

The present application claims priority from U.S. Provisional Patent Application No. 60/934,736 filed on Jun. 15, 2007, the contents of which are incorporated herein by reference in its entirety.

FIELD

This invention relates, generally, to catheters and, more particularly, to a deflectable stylet for a catheter and to a catheter including the deflectable stylet.

Background

In the field of cardiac procedures, use is made of a catheter that is steered through a patient's vasculature and is then placed at the desired site. Generally, the site is within a heart of a patient and a distal part of the catheter needs to be maneuvered into position against heart wall tissue. To be able to manipulate the distal part of the catheter to place it in tissue contact, the end of the catheter is flexible. A deflectable stylet is associated with the catheter for deflecting the distal part of the catheter.

Often, the part of the heart wall that needs to be accessed is awkwardly situated, resulting in it being difficult to place the distal part of the catheter in contact with the desired part of the tissue to be treated or diagnosed.

SUMMARY

According to a first aspect of the invention, there is provided a deflectable stylet for a catheter, the stylet including:
  an elongate deflectable member with a bend-enhancing region defined at a distal part of the deflectable member;
  an actuator having a distal end fast with a distal end of the deflectable member, relative displacement between the actuator and the deflectable member causing deflection of the distal part of the deflectable member at the bend-enhancing region; and
  a control member displaceably arranged relative to the deflectable member, the control member interacting with the bend-enhancing region of the deflectable member for controlling the extent of deflection of the distal part of the deflectable member.

By "the extent of deflection of the distal part of the deflectable member" is generally meant that the size of the radius of curvature of the deflected distal part of the deflectable member. However, the deflectable member may be able to be deflected in ways other than into a curved shape, for example, into a helical shape and the control member may be operable to control the shape of such helical deflection and the terminology "the extent of deflection of the distal part of the deflectable member" is intended to cover such applications as well as other applications.

The bend-enhancing region of the deflectable member may be defined by a plurality of longitudinally spaced, transversely extending slots formed in the distal part of the deflectable member. The slots may be arranged in groups. The spacing between the slots of one group may differ with respect to the spacing between the slots of at least one other group. Thus, for example, the slots may be arranged in three groups. The slots in the most distal group may be closer together than the slots in the middle group and the slots in the middle group may be closer together than the slots in the most proximal group.

The control member may be configured to impede the bend-enhancing region of the deflectable member for controlling the extent of deflection of the distal part of the deflectable member.

In one embodiment, the deflectable member may comprise an elongate tubular member defining a passage with the control member being a tube received in the passage of the tubular member and the control member and the tubular member being slidably displaceable relative to each other to control the extent of deflection of the distal part of the deflectable member. In another embodiment, the deflectable member may comprise an elongate tubular member defining a passage with the control member being a sleeve received over the tubular member and the control member and the tubular member being slidably displaceable relative to each other to control the extent of deflection of the distal part of the deflectable member.

The actuator may be a pull wire. The pull wire may be received in the passage of the tubular member.

The control member may impart torsional stiffness to the deflectable member. However, there may be embodiments where the control member provides insufficient torsional stiffness to the deflectable member. In such circumstances, the stylet may include a stiffening element for imparting torsional stiffness to the deflectable member.

The stylet may include a deflection control mechanism connectable to a catheter handle, the deflection control mechanism controlling relative axial displacement of the deflectable member, the actuator and the control member relative to each other.

The deflection control mechanism may include a body member and a mounting formation for engaging a complementary receiving formation of the catheter handle, the mounting formation being displaceably arranged relative to the body member and the mounting formation acting on a deflection control element of the catheter handle and further mounting one of the deflectable member and the actuator. The body member of the deflection control mechanism may define an anchoring formation for anchoring the other of the actuator and the deflectable member.

The deflection control mechanism may further include a mounting member displaceably arranged relative to the body member, the mounting member mounting a proximal end of the control member.

Preferably, the stylet is a disposable item. Thus, the components of the stylet may be of low cost materials. For example, the deflectable member may be of a low cost plastics material, such as PEEK. The control member and the actuator may be of a steel material, such as a stainless steel.

According to a second aspect of the invention, there is provided a catheter assembly which includes:
  a handle having a handle body;
  an electrode sheath extending from a distal end of the handle body, the electrode sheath defining a lumen; and
  a deflectable stylet, as described above, arranged within the lumen of the electrode sheath.

The handle body may define a receiving formation for receiving an attachment formation of the deflection control mechanism of the stylet.

The handle may include a deflection control member displaceably arranged relative to the handle body, the deflection control member including the engaging formation to be engaged by the mounting formation of the deflection control mechanism. The handle may further include a projection control member displaceably arranged on the handle body for controlling projection of the electrode sheath relative to the stylet. The control member of the stylet may be received in the lumen of the electrode sheath, over the deflectable member, for imparting torsional stiffness to the deflectable member and to the electrode sheath.

BRIEF DESCRIPTION OF THE DRAWINGS

FIG. 2A shows a side view of a part of the stylet;

FIG. 2B shows a side view of a part of the stylet according to an alternative embodiment of the deflectable stylet;

FIG. 3 shows a side view of a deflectable member of the stylet;

FIG. 4 shows, on an enlarged scale, a cross-sectional end view of the deflectable member taken along line IV-IV in FIG. 3;

FIG. 5 shows a cross-sectional side view of the stylet;

FIG. 6 shows, on an enlarged scale, the part of the stylet surrounded by circle 'A' in FIG. 5;

FIG. 7 shows, on an enlarged scale, the part of the stylet surrounded by circle 'B' in FIG. 5;

FIG. 10 shows a sectional side view of the part of the catheter in its deflected configuration;

FIG. 11 shows, on an enlarged scale, the part of the catheter surrounded by circle 'D' in FIG. 10.

DETAILED DESCRIPTION

Figure 1:
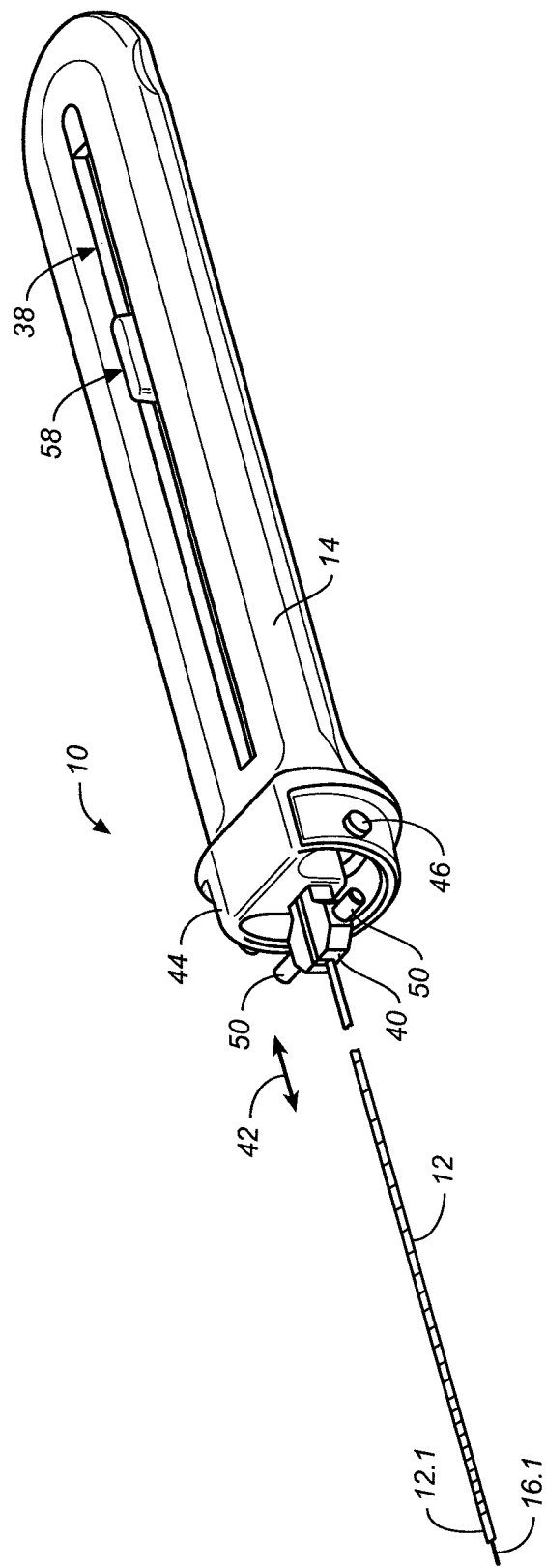
FIG. 1 shows a three dimensional view of an embodiment of a deflectable stylet.

In the drawings, reference 10 generally designates an embodiment of a deflectable stylet for a catheter. The deflectable stylet 10 includes an elongate deflectable member in the form of a sleeve 12 extending from a distal end of a deflection control mechanism 14. The sleeve 12 defines a passage 13 (FIG. 4). The stylet 10 further includes an actuator in the form of a pull wire 16. The pull wire 16 is received sleeve 12. A distal end 16.1 of the pull wire 16 is fast with a distal end 12.1 of the sleeve 12. A control member in the form of a tube 18 is received over the pull wire 16 and is received in the passage 13 of the sleeve 12, as will be described in greater detail below.

The sleeve 12 is of a synthetic plastics material, more particularly, a polyetheretherketone (PEEK) plastics material.

A bend-enhancing region 20 (FIG. 2A) is defined at a distal part 12.2 of the sleeve 12. The bend-enhancing region 20 comprises a plurality of longitudinally spaced, transversely extending slots 22 (FIGS. 3 and 4) formed within a wall of the sleeve 12. The slots 22 are formed, for example, by laser cutting a wall of the sleeve 12. As illustrated most clearly in FIG. 4 of the drawings, each slot 22 subtends an angle of less than 180°, more particularly about 150°. It will, however, be appreciated that each slot 22 could subtend an angle greater than 180° and this would, to a greater or a lesser extent be dependent on the material from which the sleeve 12 is made. In this specification, the term "subtend," unless the context clearly indicates otherwise, is used in the sense of forming or marking the limits of the angle.

The slots 22 are arranged in spaced groups 24, 26 and 28. While three groups 24-28 are illustrated, it will be appreciated that the slots 22 could be arranged in a greater or a fewer number of groups as desired.

The group 24 of slots has the slots 22 spaced more closely than the slots 22 of the group 26. Similarly, the slots 22 of the group 26 are spaced more closely together than the slots 22 of the group 28.

Figure 12:
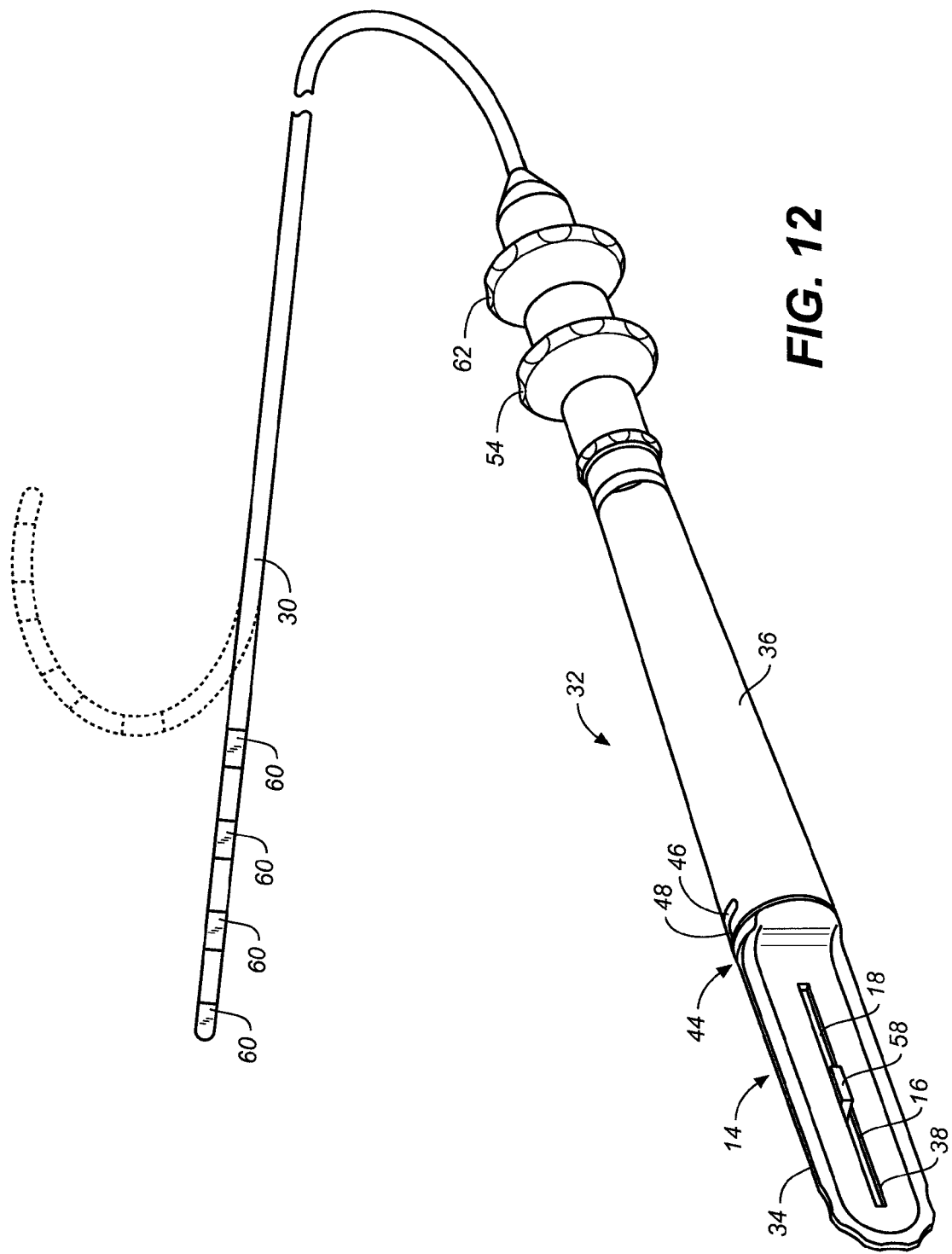
FIG. 12 shows a three dimensional view of the catheter assembly.

The tube 18 is slidable relative to the sleeve 12 to occlude a greater or a fewer number of slots 22. When the tube 18 is closer to the distal end 12.1 of the sleeve 12, the slots 22 of the group 24 are not occluded by the tube 18. By urging the sleeve 12 distally relative to the pull wire 16, a small radius of curvature deflection of the distal part 12.2 of the sleeve 12 occurs. When the tube 18 is pulled proximally relative to the sleeve 12 to expose the slots 22 of the group 26, a larger radius of curvature deflection of the distal part 12.2 of the sleeve 12 occurs by urging the sleeve 12 distally with respect to the pull wire 16. Further, when the tube 18 is pulled proximally further relative to the sleeve 12 to expose the slots 22 of the group 28, a still larger radius of curvature deflection of the distal part 12.2 of the sleeve 12 occurs when the sleeve 12 is urged distally relative to the pull wire 16. Thus, by varying the position of the tube 18 relative to the sleeve 12, a variable deflection of the distal part 12.2 of the sleeve 12 and, accordingly, a distal part of an electrode sheath 30 (FIG. 12) of a catheter 32 in which the stylet 10 is received occurs. This creates greater flexibility and versatility enabling a clinician more accurately to position a distal part of the electrode sheath 30 of the catheter 32. In the alternative embodiment illustrated in FIG. 2B, the tube 18 is received over the sleeve 12, wherein the tube 18 and the sleeve 12 are slidably displaceable relative to each other to control the extent of deflection of the distal part of the sleeve 12.

The tube 18 and the pull wire 16 are of a low cost material, such as a stainless steel. Thus, the stylet 10, being made of low cost material, is a one-use product and can be disposed of after a single use.

The deflection control mechanism 14 includes a body member 34 mountable to a proximal end of a handle body 36 of the catheter 32. The body member 34 has a longitudinally extending slot 38 defined in it in which the pull wire 16 is receivable as shown more clearly in FIG. 5 of the drawings.

A distal end of the body member 34 carries a mounting formation 40. The mounting formation 40 is displaceable axially relative to the body member 34 in the direction of arrows 42. The mounting formation 40 has a proximal end of the sleeve 12 connected to it.

Figure 9:
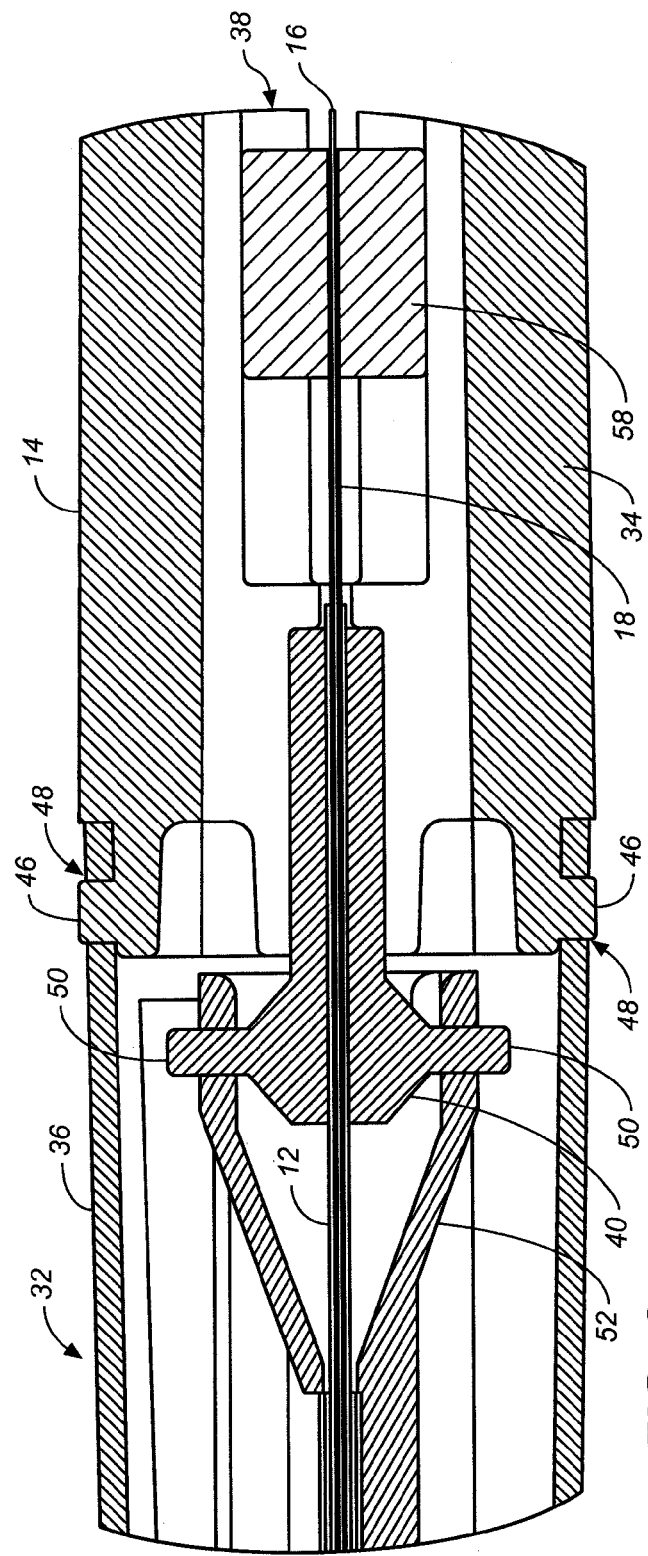
FIG. 9 shows, on an enlarged scale, the part of the catheter surrounded by circle 'C' in FIG. 8.

A boss 44 is arranged at a distal end of the body member 34. An attachment formation in the form of a pair of opposed, radially outwardly extending pins 46 (FIG. 9) is carried by the boss 44. These pins 46 are received in complementary receiving formations 48 in the handle body 36 of the catheter 32. As shown more clearly in FIG. 12, each receiving formation 48 is in the form of an L-shaped slot in the proximal end of the handle body 36 so that the body member 34 of the displacement control mechanism 14 is attached to the handle 36 bayonet fashion.

Similarly, the mounting formation 40 carries a pair of diametrically opposed, outwardly extending mounting pins 50. The mounting pins 50, in turn, engage a slide 52 (FIGS. 8-11). The slide 52 is connected to a displacement control member or knob 54 displaceably arranged on the handle body 36 of the catheter 32. The displacement control member 54 is used to displace the mounting formation 40 in the direction of arrows 42. In so doing, the sleeve 12 is displaced relative to the pull wire 16 to effect deflection of the distal part 12.2 of the sleeve 12.

Figure 8:
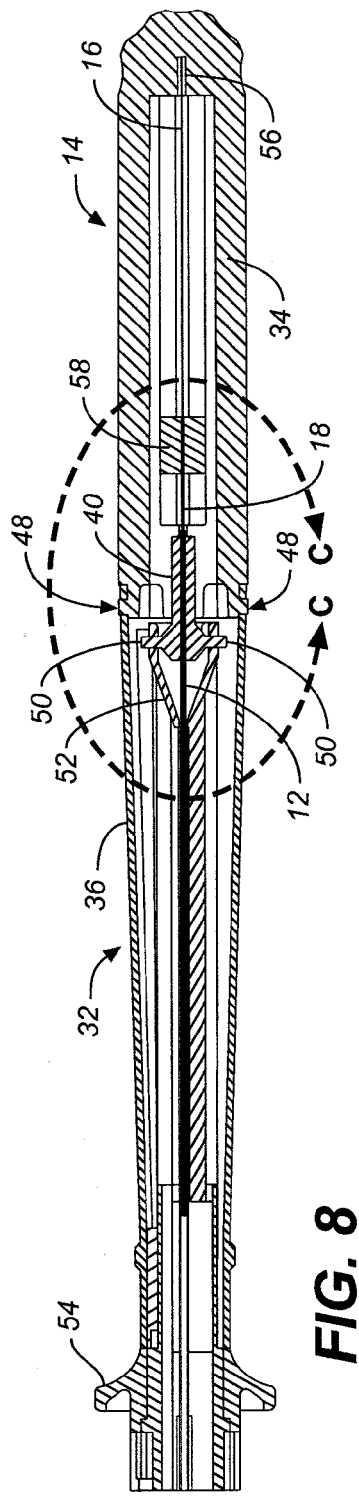
FIG. 8 shows a sectional side view of an embodiment of a part of a catheter in its non-deflected configuration.

The pull wire 16 is anchored within the body member 34 of the displacement control mechanism 14 at a proximal end of the body member 34. Thus, as shown in FIGS. 8 and 10 of the drawings, a proximal end of the pull wire is anchored at 56 at a proximal end of the body member 34 of the deflection control mechanism 14.

A slider 58 is received in the slot 38 of the body member 34 of the deflection control mechanism 14. The tube 18 is attached to the slider 58 for effecting displacement of the tube 18 relative to the sleeve 12. Thus, by sliding the distal end of the tube 18 relative to the sleeve 12, as described above, the selected radius of curvature of deflection of the distal part 12.2 of the sleeve 12 can be achieved.

In FIGS. 8-12 of the drawings, an embodiment of a catheter 32 is illustrated. The catheter 32 includes the electrode sheath 30 attached to a distal end of the handle body 36. The electrode sheath 30 of the catheter 32 is fabricated to have an unimpeded lumen. This is achieved by having conductors (not shown) for electrodes 60 carried at the distal end of the electrode sheath 30 embedded in a wall of the electrode sheath 30. The deflectable stylet 10 is thus received within the lumen of the electrode sheath 30 to effect deflection of the distal part of the electrode sheath 30 as described above.

The catheter 32 further includes a projection control member 62 arranged distally of the displacement control member 54. The projection control member 62 is used to project the distal part of the electrode sheath 30 relative to the distal part 12.2 of the deflectable stylet 10 to extend the reach of the electrode sheath 30 further. This further improves the versatility of the catheter 32 using the deflectable stylet 10. With this arrangement, a variable radius of curvature can be achieved plus the distal part of the electrode sheath 30 can be projected relative to the distal part 12.2 of the sleeve 12 of the stylet 10 to enable the electrode sheath 30 to access awkward to reach places in a patient's heart.

In the embodiment described above with reference to FIGS. 1-7 of the drawings, the stylet 10 has been described as having the tube 18 within the passage 13 of the sleeve 12. In another embodiment, the tube 18 could, instead, be arranged outwardly of the sleeve 12. In this embodiment, the tube 18 is received within the lumen of the electrode sheath 30 of the catheter 32 separately or as part of the deflectable stylet 10 with the sleeve 12 and its pull wire 16 being received within the tube 18. The effect of having the tube outside the sleeve 12 is the same as having the tube 18 within the passage 13 of the sleeve 12. Thus, the variability of the radius of curvature of the distal part 12.2 is still controlled by manipulating the position of the tube 18 relative to the sleeve 12 using the slider 58 of the displacement control mechanism 14.

Hence, it is an advantage of the invention that a deflectable stylet 10 is provided which has an adjustable radius of curvature of its distal part 12.2. This improves the versatility of a catheter 32 in which the deflectable stylet 10 is received and gives the clinician more scope to maneuver and position the distal part of the electrode sheath 30 of the catheter 32. Further, by using the projection control member 62 of the catheter 32, the versatility of the catheter 32 and the ability to position the distal part of the electrode sheath 30 of the catheter 32 at a desired location in a patient's heart is enhanced. In addition, the deflectable stylet 10 is made of low cost material rendering it suitable for one-use applications without significant cost penalties.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A deflectable stylet for a catheter, the deflectable stylet including:
    an elongate deflectable member with a bend-enhancing region defined at a distal part of the elongate deflectable member;
    an actuator having a distal end fast with a distal end of the elongate deflectable member, relative displacement between the actuator and the elongate deflectable member causing deflection of the distal part of the elongate deflectable member at the bend-enhancing region;
    a control member axially displaceable relative to the elongate deflectable member, wherein the control member inhibits bending of a longitudinally overlapping portion of the bend-enhancing region, wherein axial displacement of the control member controls the extent of longitudinal overlap between the control member and the bend-enhancing region; and
    a deflection control mechanism connectable to a proximal end of a catheter handle of the catheter, the deflection control mechanism being coupled to the control member thereby to control axial displacement of the control member relative to the elongate deflectable member, the deflection control mechanism being further coupled to the actuator, wherein the deflection control mechanism is configured to be selectively detachable from and re-attachable with the proximal end of the catheter handle, and the deflection control mechanism further comprises:
        a mounting formation mounting one of the elongate deflectable member and the actuator to the deflection control mechanism; and
        an anchoring formation anchoring the other of the elongate deflectable member and the actuator to the deflection control mechanism, wherein the mounting formation is displaceably arranged relative to the deflection control mechanism and the anchoring formation during use of the deflectable stylet.

2. The deflectable stylet of claim 1, wherein the bend-enhancing region of the elongate deflectable member is defined by a plurality of longitudinally spaced, transversely extending slots formed in the distal part of the elongate deflectable member.

3. The deflectable stylet of claim 2, wherein the slots are arranged in groups.

4. The deflectable stylet of claim 3, wherein the spacing between the slots of one group differs with respect to the spacing between the slots of at least one other group.

5. The deflectable stylet of claim 1, wherein the elongate deflectable member comprises an elongate tubular member defining a passage, the control member is a tube received in the passage of the elongate tubular member, and the control member and the elongate tubular member are slidably displaceable relative to each other to control the extent of longitudinal overlap between the control member and the bend-enhancing region.

6. The deflectable stylet of claim 5, wherein the actuator is a pull wire.

7. The deflectable stylet of claim 6, wherein the pull wire is received in the passage of the elongate tubular member.

8. The deflectable stylet of claim 1, wherein the elongate deflectable member comprises an elongate tubular member defining a passage, and wherein the control member is a sleeve disposed over the elongate tubular member, the control member and the elongate tubular member are slidably displaceable relative to each other to control the extent of longitudinal overlap between the control member and the bend-enhancing region.

9. The deflectable stylet of claim 8, wherein the actuator is a pull wire.

10. The deflectable stylet of claim 9, wherein the pull wire is received in the passage of the elongate tubular member.

11. The deflectable stylet of claim 1, further including a stiffening element for imparting torsional stiffness to the elongate deflectable member.

12. The deflectable stylet of claim 1, wherein the deflection control mechanism further comprises a body member defining a distal end of the deflection control mechanism, the distal end of the deflection control mechanism including an attachment formation for engaging a complementary receiving formation of the catheter handle, the complementary receiving formation located at a proximal end of the catheter handle.

13. The deflectable stylet of claim 12, wherein the body member of the deflection control mechanism includes the anchoring formation.

14. The deflectable stylet of claim 12, wherein the deflection control mechanism comprises a slider displaceably arranged relative to the body member, the slider coupled to a proximal end of the control member such that the displacement of the slider relative to the body member causes the axial displacement of the control member.

15. The deflectable stylet of claim 14, wherein the complementary receiving formation of the catheter handle comprises a pair of L-shaped slots.

16. The deflectable stylet of claim 15, wherein the attachment formation of the deflection control mechanism comprises a first pair of mounting pins removably fastenable with the pair of L-shaped slots at the proximal end of the catheter handle.

17. The deflectable stylet of claim 16, wherein the first pair of mounting pins are located on a boss arranged at a distal end of the body member of the deflection control mechanism.

18. The deflectable stylet of claim 16,
wherein the mounting formation of the deflection control mechanism comprises a second pair of mounting pins, the second pair of mounting pins being coupled to a displaceable slide of the catheter handle, wherein the slide is operatively joined to a displacement control knob displaceably arranged on the catheter handle, and wherein the displacement control knob is configured to axially displace the mounting formation.

19. A catheter assembly, including:
a handle having a handle body;
an electrode sheath extending from a distal end of the handle body, the electrode sheath defining a lumen; and
a deflectable stylet arranged within the lumen of the electrode sheath, wherein the deflectable stylet includes:
an elongate deflectable member with a bend-enhancing region defined at a distal part of the elongate deflectable member;
an actuator having a distal end fast with a distal end of the elongate deflectable member, relative displacement between the actuator and the elongate deflectable member causing deflection of the distal part of the elongate deflectable member at the bend-enhancing region;
a control member axially displaceable relative to the elongate deflectable member, wherein the control member inhibits bending of a longitudinally overlapping portion of the bend-enhancing region, wherein axial displacement of the control member controls the extent of longitudinal overlap between the control member and the bend-enhancing region; and
a deflection control mechanism connectable to a proximal end of the handle, the deflection control mechanism being coupled to the control member thereby to control axial displacement of the control member relative to the elongate deflectable member, the deflection control mechanism being additionally coupled to the actuator, wherein the deflection control mechanism is configured to be selectively detachable from and re-attachable with the proximal end of the handle, and the deflection control mechanism further comprises:
a mounting formation mounting one of the elongate deflectable member and the actuator to the deflection control mechanism; and
an anchoring formation anchoring the other of the elongate deflectable member and the actuator to the deflection control mechanism, wherein the mounting formation is displaceably arranged relative to the deflection control mechanism and the anchoring formation during use of the deflectable stylet.

20. The catheter assembly of claim 19, wherein the deflection control mechanism further comprises a body member defining an attachment formation for engaging a complementary receiving formation of the handle.

21. The catheter assembly of claim 20, wherein the mounting formation is additionally displaceably arranged relative to the handle body.

22. The deflectable stylet of claim 21, wherein the body member comprises a first pair of mounting pins for engaging an outer housing of the complementary receiving formation, and wherein the mounting formation comprises a second pair of mounting pins for engaging a slide of an inner portion of the handle, the first pair of mounting pins and the second pair of mounting pins being configured to effect detachment and re-attachment of the deflection control mechanism and the handle.

23. The catheter assembly of claim 21, wherein the handle further includes a projection control member displaceably arranged on the handle body for controlling projection of the electrode sheath relative to the deflectable stylet.

24. The catheter assembly of claim 20, wherein the control member of the deflectable stylet is received in the lumen of the electrode sheath, the control member is disposed over the elongate deflectable member, and the control member is configured for imparting torsional stiffness to the elongate deflectable member and to the electrode sheath.

25. The catheter assembly of claim 20, wherein the elongate deflectable member comprises an elongate tubular member defining a passage, the control member is a tube received in the passage of the elongate tubular member, and the control member and the elongate tubular member are slidably displaceable relative to each other to control the extent of longitudinal overlap between the control member and the bend-enhancing region.

26. The catheter assembly of claim 25, wherein the actuator is a pull wire received in the passage of the elongate tubular member.

27. A deflectable stylet for a catheter, the deflectable stylet including:
an elongate deflectable member with a bend-enhancing region defined at a distal part of the elongate deflectable member;
an actuator having a distal end fast with a distal end of the elongate deflectable member, relative displacement between the actuator and the elongate deflectable member causing deflection of the distal part of the elongate deflectable member at the bend-enhancing region;

a control member axially displaceable relative to the elongate deflectable member, wherein the control member inhibits bending of a longitudinally overlapping portion of the bend-enhancing region, wherein axial displacement of the control member controls the extent of longitudinal overlap between the control member and the bend-enhancing region; and a deflection control mechanism connectable to a proximal end of a catheter handle of the catheter, the deflection control mechanism being coupled to the control member thereby to control axial displacement of the control member relative to the elongate deflectable member, the deflection control mechanism being further coupled to the actuator, a distal end of the deflection control mechanism including a first pair of mounting pins removably fastenable with a pair of complementary L-shaped slots at the proximal end of the catheter handle; and a mounting formation displaceably coupled to the distal end of the deflection control mechanism, the mounting formation comprising a second pair of mounting pins configured to be coupled to a displaceable slide of the catheter handle, wherein the slide is operatively joined to a displacement control knob displaceably arranged on the catheter handle, and the displacement conrol knob is configured to axially displace the mounting formation.

* * * * *

UNITED STATES PATENT AND TRADEMARK OFFICE
CERTIFICATE OF CORRECTION

PATENT NO. : 8,506,562 B2  
APPLICATION NO. : 12/136707  
DATED : August 13, 2013  
INVENTOR(S) : Neil L. Anderson and David Ogle Page 1 of 1

It is certified that error appears in the above-identified patent and that said Letters Patent is hereby corrected as shown below:

On the title page:
In ITEM (57) ABSTRACT:  change "end. 1 fast" to --end fast--

In the claims:
| | | | |
|---|---|---|---|
| CLAIM 22, | COLUMN 8, | LINE 30, | change "deflectable stylet" to --catheter assembly-- |
| CLAIM 25, | COLUMN 8, | LINE 50, | change "of claim 20," to --of claim 19,-- |

Signed and Sealed this  
Nineteenth Day of April, 2016

Michelle K. Lee  
*Director of the United States Patent and Trademark Office*